(12) United States Patent
Tanimura et al.

(10) Patent No.: US 10,502,627 B2
(45) Date of Patent: Dec. 10, 2019

(54) COLOR MEASURING DEVICE AND COLOR MEASURING METHOD

(71) Applicant: KONICA MINOLTA, INC., Chiyoda-ku (JP)

(72) Inventors: Yasutaka Tanimura, Nara (JP); Ryoji Bando, Sakai (JP)

(73) Assignee: Konica Minolta, Inc., Tokyo (JP)

( * ) Notice: Subject to any disclaimer, the term of this patent is extended or adjusted under 35 U.S.C. 154(b) by 55 days.

(21) Appl. No.: 15/563,852

(22) PCT Filed: Mar. 28, 2016

(86) PCT No.: PCT/JP2016/059988
§ 371 (c)(1),
(2) Date: Oct. 2, 2017

(87) PCT Pub. No.: WO2016/163266
PCT Pub. Date: Oct. 13, 2016

(65) Prior Publication Data
US 2018/0080829 A1 Mar. 22, 2018

(30) Foreign Application Priority Data
Apr. 6, 2015 (JP) ................................. 2015-077705

(51) Int. Cl.
G01J 3/52 (2006.01)
G01J 3/46 (2006.01)
(Continued)

(52) U.S. Cl.
CPC . *G01J 3/52* (2013.01); *G01J 3/46* (2013.01); *G01J 3/462* (2013.01); *G01J 3/524* (2013.01); *G01N 21/251* (2013.01); *G01N 21/255* (2013.01); *G06T 7/90* (2017.01); *G01N 2201/1042* (2013.01)

(58) Field of Classification Search
CPC ............... G01J 3/52; G01J 3/524; G01J 3/462
See application file for complete search history.

(56) References Cited

U.S. PATENT DOCUMENTS 2,729,898 A * 1/1956 Rahr .................. G01J 3/52 434/98
6,262,804 B1 * 7/2001 Friend .................. G01J 3/02 235/462.45

(Continued)

FOREIGN PATENT DOCUMENTS

JP 2000-253262 9/2000
JP 2003-216398 7/2003
(Continued)

Primary Examiner — Kara E. Geisel
Assistant Examiner — Rufus L Phillips
(74) Attorney, Agent, or Firm — Cozen O'Connor

(57) ABSTRACT

A color measuring device and a color measuring method according to the present invention includes an imaging unit, a first image of a color chart and a second image accompanied with the color chart are obtained by the imaging unit, the second image being a predetermined code indicating control information about the color measuring device, the control information is obtained based on the obtained second image, and operation of the color measuring device is controlled based on the obtained control information.

10 Claims, 9 Drawing Sheets

(51) Int. Cl.
    *G06T 7/90*           (2017.01)
    *G01N 21/25*        (2006.01)

(56)           References Cited

U.S. PATENT DOCUMENTS

| | | | |
|---|---|---|---|
| 6,717,673 B1* | 4/2004 | Janssen | G01J 3/46 |
| | | | 356/402 |
| 6,765,674 B2* | 7/2004 | Orelli | G01J 3/02 |
| | | | 356/402 |
| 2002/0140985 A1* | 10/2002 | Hudson | G06K 15/00 |
| | | | 358/3.23 |
| 2003/0063275 A1* | 4/2003 | Hubble, III | G01J 3/50 |
| | | | 356/402 |
| 2004/0008207 A1* | 1/2004 | Dornan | G01J 3/52 |
| | | | 345/589 |
| 2005/0243317 A1* | 11/2005 | Baker | G01J 3/50 |
| | | | 356/402 |
| 2007/0291291 A1* | 12/2007 | Vilar | H04N 1/3878 |
| | | | 358/1.9 |
| 2007/1029129 | 12/2007 | Vilar et al. | |
| 2009/0033954 A1* | 2/2009 | Bray | H04N 1/6033 |
| | | | 358/1.9 |
| 2009/1003395 | 2/2009 | Bray | |

FOREIGN PATENT DOCUMENTS

| | | |
|---|---|---|
| JP | 2004-23643 | 1/2004 |
| JP | 2006-157207 | 6/2006 |
| JP | 2009-35000 | 2/2009 |
| JP | 2010-226580 | 10/2010 |

* cited by examiner

EDGE LINE(—), INTERMEDIATE LINE(⋯), AND PATCH CENTER POSITION(○)

COLOR MEASURING DEVICE AND COLOR MEASURING METHOD

RELATED APPLICATIONS

This is a U.S. National Phase Application under 35 USC 371 of International Application PCT/JP2016/059988 filed on Mar. 28, 2016.

This application claims the priority of Japanese application no. 2015-077705 filed Apr. 6, 2015, the entire content of which is hereby incorporated by reference.

TECHNICAL FIELD

The present invention relates to a color measuring device and a color measuring method for measuring color, particularly to a color measuring device and a color measuring method for being able to obtain control information indicated by a code and control operation based on the obtained control information.

BACKGROUND ART

In a company, such as a printing company, which generates a color printed matter, color of the printed matter is periodically measured and color of a printing device that prints the printed matter is adjusted in order to keep quality of the printed matter. In the color adjustment of the printing device, for example, original image data called a color chart is printed by the printing device, and color of each patch in the printed color chart is measured by the color measuring device. A color shift amount between a measured value of the color of each patch and a target value of the color of each patch is evaluated, and the color of the printing device is adjusted according to an evaluation result.

The color chart includes a plurality of color samples called the patches, each of the plurality of patches is formed by a different color (hue, lightness, and saturation) in many cases, and the plurality of patches are arrayed in a predetermined mode. There are various color charts. For example, there is a color chart having a mode formed by two-dimensionally arraying a plurality of square patches having various colors. In the color chart of the mode, there are various patterns. For example, the patches are arrayed such that a random color arrangement is obtained depending on a content to be evaluated, or the patches are arrayed such that a change in shade between the patches adjacent to each other is decreased like gradation. Not only such color charts are produced by a user using a color chart production tool provided from a manufacturer of the color measuring device, but also the color charts are provided from a public institution. Thus, in the color chart, there are various patterns depending on a shape, a disposition, and a color scheme of the patch.

On the other hand, the number of colors used in the color adjustment of the printing device increases year by year, the number of patches disposed in the color chart also increases with increasing number of colors, and a size (area) of each patch is small. There is also a set chart including plurality of color charts.

Due to such circumstances, it is actually impossible that the colorimetry is performed while a measurement region of the color measuring device is accurately positioned by hand with respect to each patch. Therefore, there is a demand for an automatic system, in which the position of each patch is automatically measured and the color of each patch is measured while the measurement region of the color measuring device is automatically matched with the measured position of each patch. There is a technology, which is disclosed in Patent Literature 1 and related to matching of color printing job output of the printing system, as an example of the system. The system disclosed in Patent Literature 1 is a system for matching of a color printing job of the printing system, and includes a plurality of image marking engines, a first test image on a medium document, the first test image being printed by a first image marking engine and having a data glyph and a plurality of reference patches, and a second test image on the medium document, the second test image being printed by a second image marking engine and having the data glyph and the plurality of reference patches. The first test image and the second test image are printed on an identical surface of the medium document, and the system disclosed in Patent Literature 1 includes an image capturing device that scans the medium document. The scanned first test image and second test image provide calibration data for matching of color correction tables of the first image marking engine and the second image marking engine, and the data glyph and the reference patch of the scanned image data are compared to the retrieved color correction tables and generates a compensation value based on a difference between the scanned image setup data and the color correction table of at least an image document next to a first image document on the first image marking engine or the second image marking engine. The data glyph can include a xerograph, an image path, and other important settings (see Paragraph 0020 in Patent Literature 1). The data glyph can include an image setting, a xerograph setting, a rendering option, transfer/medium-related adjustment, and other printing job attributes (see Paragraph 0022 in Patent Literature 1). The data glyph includes pieces of information such as time, date, a serial number of a machine, a master image name, and a master image serial number (see Paragraph 0034 in Patent Literature 1).

In the system disclosed in Patent Literature 1, a scanner is disposed as output of the system, and the data glyph is detected and interpreted by the scanner (see Paragraphs 0012 and 0025 in Patent Literature 1). Therefore, in the system disclosed in Patent Literature 1, it is necessary to prepare the scanner separated from the system, and it is necessary to input information about the data glyph interpreted by the scanner to the system, whereby the system becomes complicated. When a user forgets to input the information about the data glyph interpreted by the scanner to the system, the user cannot use the information about data glyph in the system.

CITATION LIST

Patent Literature

Patent Literature 1: Unexamined Japanese Patent Publication No. 2009-35000

SUMMARY OF INVENTION

The present invention has been made in view of the above-described circumstances, and an object thereof is to provide a color measuring device and a color measuring method, in which the code control information can surely be used with a simple configuration.

A color measuring device and a color measuring method according to the present invention includes an imaging unit, a first image of a color chart and a second image accompanied with the color chart are obtained by the imaging unit, the second image being a predetermined code indicating control information about the color measuring device, the control information is obtained based on the obtained second image, and operation of the color measuring device is controlled based on the obtained control information. Accordingly, in the color measuring device and color measuring method of the present invention, the code information can surely be used with a simple configuration.

The above and other objects, features, and advantages of the present invention will appear more fully from the following detailed description and the accompanying drawings.

DESCRIPTION OF EMBODIMENT

Hereinafter, an embodiment of the present invention will be described with reference to the drawings. The same configuration is designated by the same reference sign in each drawing, and the overlapping description is omitted as appropriate. In the description, the configuration is designated by the reference sign without a subscript when generally named, and the configuration is designated by the reference sign with a subscript when individually referred to.

Figure 1:
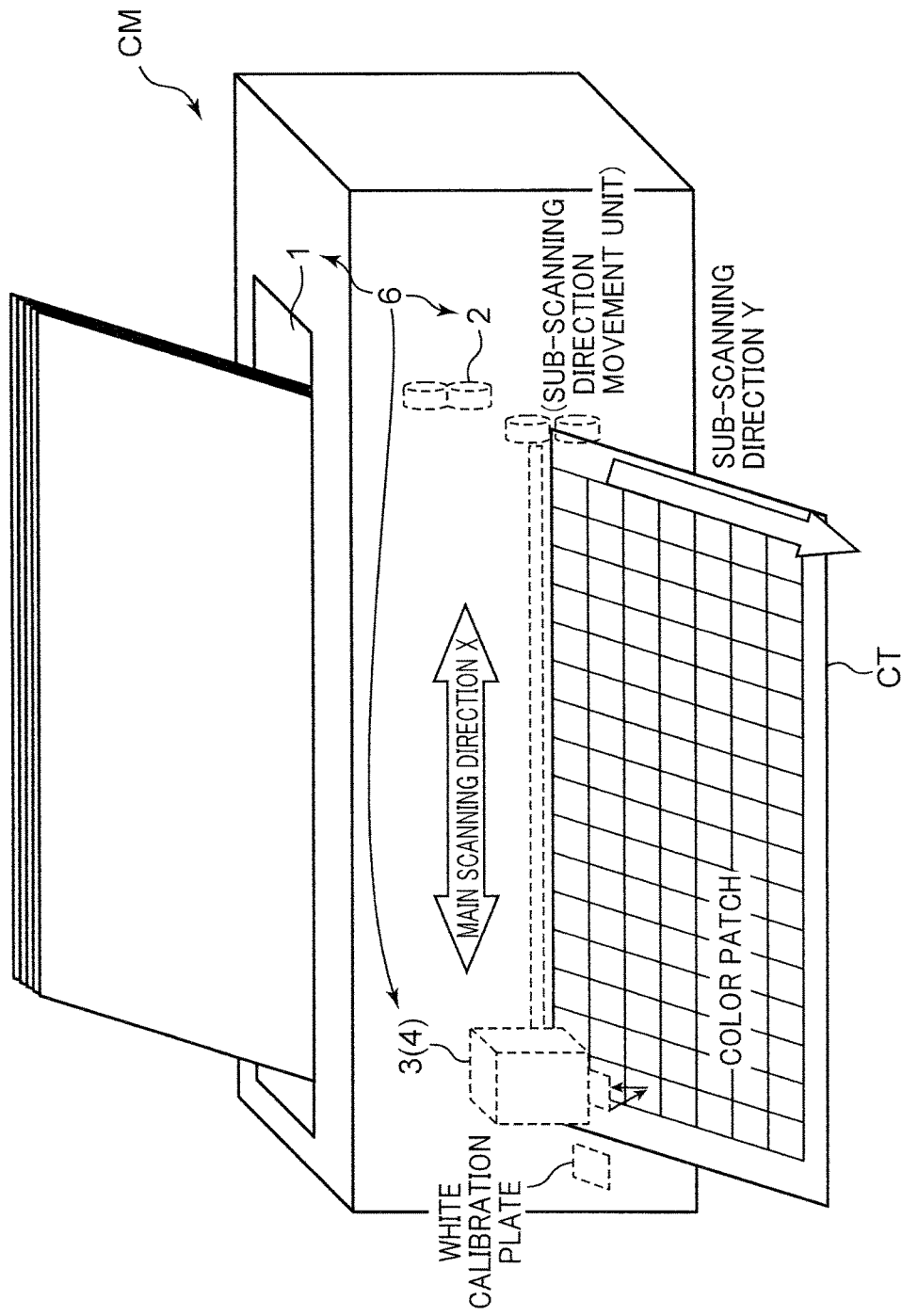
FIG. 1 is a perspective view illustrating a schematic configuration of a color measuring device according to an embodiment.
Figure 2:
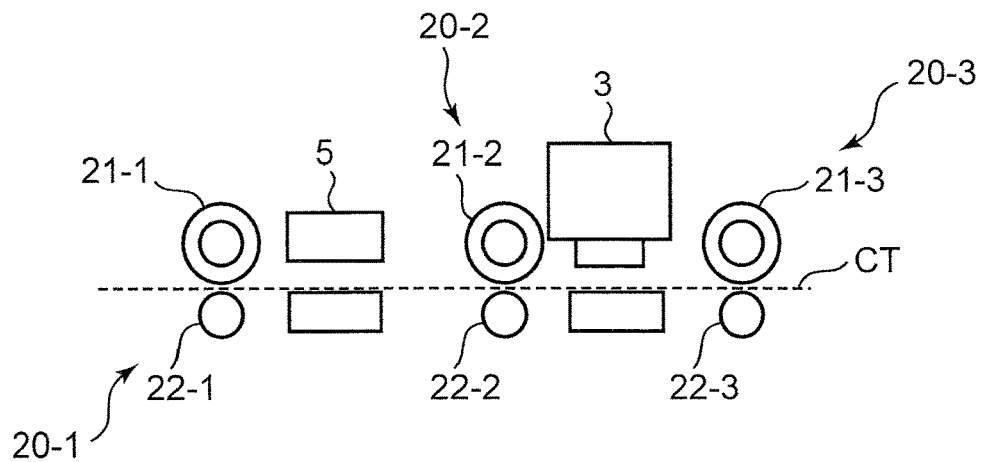
FIG. 2 is a schematic side view illustrating a disposition relationship between an imaging unit and a colorimetry unit in the color measuring device.
Figure 3:
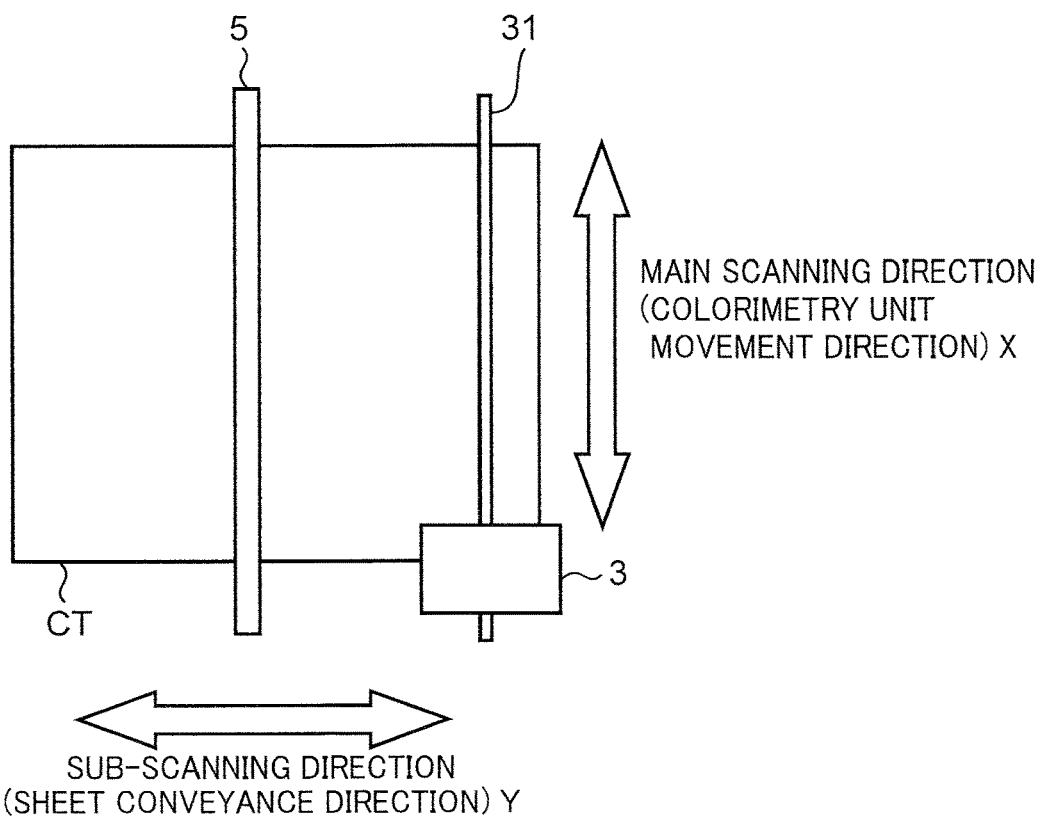
FIG. 3 is a schematic plan view illustrating the disposition relationship between the imaging unit and the colorimetry unit in the color measuring device.
Figure 4:
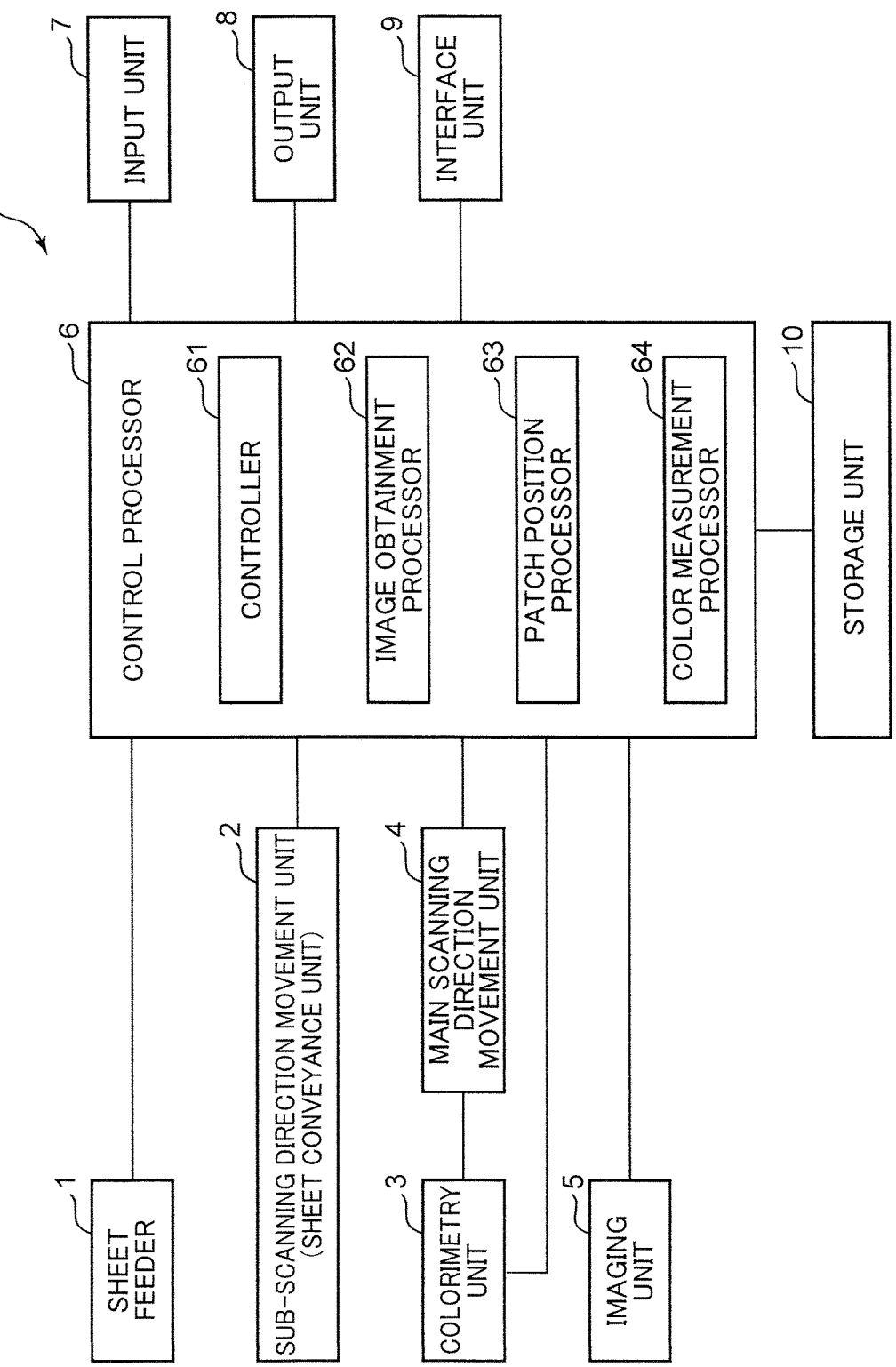
FIG. 4 is a block diagram illustrating an electric configuration of the color measuring device.

FIG. 1 is a perspective view illustrating a schematic configuration of a color measuring device according to the embodiment. FIG. 2 is a schematic side view illustrating a disposition relationship between an imaging unit and a colorimetry unit in the color measuring device according to the embodiment. FIG. 3 is a schematic plan view illustrating the disposition relationship between the imaging unit and the colorimetry unit in the color measuring device according to the embodiment. FIG. 4 is a block diagram illustrating an electric configuration of the color measuring device according to the embodiment.

A color measuring device CM of the embodiment measures color (hue, lightness, and saturation) of a measurement object that is of a color measurement target. For example, as illustrated in FIGS. 1 to 4, the color measuring device CM includes a sheet feeder 1, a sub-scanning direction movement unit (sheet conveyance unit) 2, and a colorimetry unit 3, a main scanning direction movement unit 4, an imaging unit 5, a control processor 6, an input unit 7, an output unit 8, an interface unit 9, and a storage unit 10.

The sheet feeder 1 is a sheet conveyance mechanism, which is connected to the control processor 6 and takes a sheet of the measurement object set in the color measuring device CM into the color measuring device CM under the control of the control processor 6. The sheet of the measurement object may be any sheet. For example, in the case that color of a printing device is adjusted, the sheet of the measurement object is a color chart CT including a plurality of patches that are predetermined color areas on a predetermined sheet. For example, a sheet feeder 1 includes a reservoir section in which the sheet of the measurement object is reserved, an intake unit including a pickup roller which picks up the sheet of the measurement object reserved in the reservoir section and takes the sheet of the measurement object in the color measuring device CM, and a feed unit including a conveyance roller that conveys the sheet of the measurement object taken in by the intake unit to the sub-scanning direction movement unit 2.

The sub-scanning direction movement unit (sheet conveyance unit) 2 is a sheet conveyance mechanism, which is connected to the control processor 6 and conveys a predetermined amount of sheet of the measurement object fed from the sheet feeder 1 in response to a unit conveyance instruction (second unit conveyance instruction) in a sub-scanning direction (second direction) orthogonal to a first direction previously set as a main scanning direction under the control of the control processor 6. The sub-scanning direction movement unit 2 can convey the sheet of the measurement object forwardly and backwardly along the sub-scanning direction. For example, the forward conveyance means that the sheet of the measurement object is conveyed from an upstream (the side of the sheet feeder 1) to a downstream (discharge side), and the backward conveyance means that the sheet of the measurement object is conveyed in an opposite direction of the forward conveyance, namely, from the downstream to the upstream. For example, the sub-scanning direction movement unit 2 includes a plurality sets of sheet conveyance rollers and a drive unit that rotates the sheet conveyance rollers. Each set of sheet conveyance rollers includes a driving roller rotated by the drive unit and a driven roller rotated according to the rotation of the driving roller. For example, the drive unit includes a stepping motor (sub-scanning stepping motor). In the sub-scanning direction movement unit 2 having the above configuration, when a one-pulse drive pulse (second drive pulse, an example of the second unit conveyance instruction) is input, the sub-scanning stepping motor is rotated by a predetermined angle (twenty-first angle), the driving roller is also rotated by a predetermined angle (twenty-second angle) by the rotation of the sub-scanning stepping motor, and the sheet of the measurement object is conveyed (moved) by a predetermined amount along the sub-scanning direction by the rotation of the driving roller. More specifically, in the example of FIG. 2, the sub-scanning direction movement unit 2 includes first to third sheet conveyance rollers 20-1 to 20-3. The first to third sheet conveyance rollers 20-1 to 20-3 are sequentially provided the upstream to the downstream along the sub-scanning direction. The first to third sheet conveyance rollers 20-1 to 20-3 respectively include first to third driving rollers 21-1 to 21-3 and first to third driven rollers 22-1 to 22-3. The first to third driving rollers 21-1 to 21-3 are driven by first to third stepping motors (not illustrated) that are rotated in synchronization with one another. In the forward conveyance, the sheet of the measurement object conveyed from the sheet feeder 1 is nipped between a pair of a first driving roller 21-1 and a first driven roller 22-1, and the first driving roller 21-1 is normally (for example, clockwise) rotated by the drive unit, whereby the sheet of the measurement object is conveyed from the first sheet conveyance roller 20-1 to the second sheet conveyance roller 20-2. The sheet of the measurement object conveyed to the second sheet conveyance roller 20-2 is similarly conveyed from the second sheet conveyance roller 20-2 to the third sheet conveyance roller 20-3 by the second sheet conveyance roller 20-2. The sheet of the measurement object conveyed to the third sheet conveyance roller 20-3 is similarly conveyed from the third sheet conveyance roller 20-3 to the downstream by the third sheet conveyance roller 20-3. In the backward conveyance, contrary to the forward conveyance, the first to third driving rollers 21-1 to 21-3 are reversely (in the above example, counterclockwise) rotated by the drive unit, thereby conveying the sheet of the measurement object from the downstream to the upstream.

Hereinafter, the main scanning direction (first direction) is an X-direction (horizontal direction), a coordinate axis set along the X-direction is an X-axis, the sub-scanning direction (second direction) is a Y-direction (vertical direction), and a coordinate axis set along the Y-direction is a Y-axis, and these are used as appropriate.

The colorimetry unit 3 is connected to the control processor 6, and measures the color of the measurement object under the control of the control processor 6. For example, the colorimetry unit 3 is a colorimetry sensor that obtains predetermined optical information about the measurement object in order to obtain the color of the measurement object. For example, the colorimetry unit 3 includes a spectroscopic optical element and a photoelectric conversion element, which measures reflectance (or transmittance) of each wavelength, and the colorimetry unit 3 is a spectroscopic colorimeter that measures color of an object based on the reflectance (or transmittance) of each wavelength. For example, the colorimetry unit 3 includes an optical filter and a photoelectric conversion element, which measures tristimulus values of RGB, and the colorimetry unit 3 is a tristimulus value type colorimeter that measures the color of the object based on a color difference of tristimulus values. In the colorimetry unit 3, what is called a white calibration plate (reference white plate) indicated by a broken line in FIG. 1 is measured, the white calibration plate being able to reflect a wavelength of a measurement range with high reflectance (for example, about 90% to about 99%), thereby performing white calibration.

The main scanning direction movement unit 4 is a movement mechanism, which is connected to the control processor 6 and moves the colorimetry unit 3 in each predetermined amount in response to a predetermined unit conveyance instruction (first unit conveyance instruction) in the main scanning direction (first direction) under the control of the control processor 6. For example, the main scanning direction movement unit 4 includes a guide member that guides the colorimetry unit 3, a feed mechanism, such as a rack and pinion or a feed screw, which moves the colorimetry unit 3 while the colorimetry unit 3 is guided by the guide member, and a feed mechanism drive unit, such as a stepping motor (the main scanning stepping motor), which drives the feed mechanism. For example, as illustrated in FIG. 3, the main scanning direction movement unit 4 includes a rack 31 extending along the main scanning direction and having a gear cut in a flat-plate rod, and a pinion (not illustrated) that is provided in the colorimetry unit 3 and rotated by the main scanning stepping motor, and the pinion and the rack 31 engage each other. In the main scanning direction movement unit 4 having the above configuration, when a one-pulse drive pulse (first drive pulse, an example of the first unit conveyance instruction) is input, the main scanning stepping motor is rotated by a predetermined angle (eleven angle), the pinion is also rotated by a predetermined angle (twelfth angle) by the rotation of the main scanning stepping motor, and the colorimetry unit 3 is moved by a predetermined amount in the main scanning direction along the rack 31 by the rotation of the pinion.

The imaging unit 5 is connected to the control processor 6, and images the optical image of the object under the control of the control processor 6. For example, the imaging unit 5 includes a line sensor (linear image sensor) in which a plurality of photoelectric conversion elements are arrayed along one direction. As illustrated in FIG. 3, the one direction that is of the array direction of the plurality of photoelectric conversion elements is matched with the main scanning direction (X-direction), and the imaging unit 5 is provided so as to extend along the main scanning direction (X-direction).

As illustrated in FIG. 2, the imaging unit 5 is provided between the first sheet conveyance roller 20-1 and the second sheet conveyance roller 20-2, and the colorimetry unit 3 and the main scanning direction movement unit 4 are provided such that the colorimetry unit 3 moves along the main scanning direction between the second sheet conveyance roller 20-2 and the third sheet conveyance roller 20-3. The imaging unit 5 images the sheet of the measurement object in each one line along the main scanning direction (X-direction) while the sub-scanning direction movement unit 2 conveys the sheet of the measurement object in the sub-scanning direction (Y-direction), thereby generating an image (image data) of the sheet of the measurement object. When the sub-scanning direction movement unit 2 conveys the sheet of the measurement object in the sub-scanning direction (Y-direction), a relative position Y of the sheet of the measurement object and the colorimetry unit 3 can be changed in the sub-scanning direction. When the main scanning direction movement unit 4 moves the colorimetry unit 3 in the main scanning direction (X-direction), a relative position X of the sheet of the measurement object and the colorimetry unit 3 can be changed in the main scanning direction. Therefore, the colorimetry unit 3 can move to any position (X,Y) on the sheet of the measurement object and measure the color of the position (X,Y).

Thus, in the embodiment, the colorimetry unit 3 can move only in the main scanning direction by the main scanning direction movement unit 4 with respect to the sheet of the measurement object. On the other hand, the sub-scanning direction movement unit (sheet conveyance unit) 2 moves the sheet of the measurement object along the sub-scanning direction. Accordingly, in the embodiment, the main scanning direction movement unit 4 and the sub-scanning direction movement unit 2 correspond to an example of the movement unit that relatively moves the position of the colorimetry unit 3 with respect to the sheet of the measurement object.

The input unit 7 is connected to the control processor 6, and inputs various commands such as a command issuing an instruction to measure the color of the measurement object and various pieces of data, such as an identifier of the measurement object, which are necessary for the colorimetry, to the color measuring device CM. For example, the input unit 7 is a plurality of input switches to which predetermined functions are allocated. The output unit 8 is connected to the control processor 6, and outputs the command or data input from the input unit 7 and the color of the measurement object, the color of the measurement object being measured by the color measuring device CM, under the control of the control processor 6. For example, the output unit 8 is a display device such as a CRT display, LCD, and an organic EL display, or a printing device such as a printer.

The input unit 7 and the output unit 8 may be configured with a touch panel. In the case that the input unit 7 and the output unit 8 are configured with the touch panel, for example, the input unit 7 is a resistance film type or electrostatic capacitance type position input device that detects and inputs an operation position, and the output unit 8 is a display device. In the touch panel, the position input device is provided on a display surface of the display device, a candidate of one or more input contents is displayed on the display device. When a user touches the display position where the input content to be input is displayed, the position input device detects the display position, and the display content displayed at the detected position is input to the color measuring device CM as the operation input content of the user. In the touch panel, the color measuring device CM easily dealt with by the user is provided because the user intuitively easily understands the input operation.

The interface unit 9 is connected to the control processor 6, and inputs and outputs data to and from an external device under the control of the control processor 6. Example of the interface unit 9 includes an RS-232C interface circuit that is of a serial communication system, an interface circuit in which a Bluetooth (registered trademark) standard is used, an interface circuit that conducts infrared communication of an IrDA (Infrared Data Association) standard, and an interface circuit in which a USB (Universal Serial Bus) standard is used. For example, the interface unit 9 may be a communication interface circuit that transmits and receives a communication signal to and from an external device through a communication line (network) according to a predetermined communication protocol. For example, the interface unit 9 may be a LAN (Local Area Network) card or a data communication card.

The storage unit 10 is connected to the control processor 6, and various predetermined programs and various predetermined pieces of data are stored in the storage unit 10 under the control of the control processor 6. For example, the various predetermined program includes a control processing program, which obtains (decodes) control information based on the second image of the code and controls operation of the color measuring device CM based on the obtained (decoded) control information. Examples of the control processing program include a color measurement program measuring the color of the measurement object, an image obtainment program obtaining the image of the measurement object, and a position measurement program obtaining each patch position in the color chart CT in the case that the measurement object is the color chart CT.

Examples of the various pieces of predetermined data include data necessary for execution of the predetermined program and data of a color measurement result. The storage unit 10 includes a ROM (Read Only Memory) that is of a nonvolatile storage element or an EEPROM (Electrically Erasable Programmable Read Only Memory) that is of a rewritable, nonvolatile storage element. The storage unit 10 includes a RAM (Random Access Memory) that serves as what is called a working memory of the control processor 6. The working memory stores data generated during the execution of the predetermined program.

The control processor 6 controls each unit of the color measuring device CM according to the function of the unit, and obtains the color of the measurement object. For example, the control processor 6 includes a CPU (Central Processing Unit) and a peripheral circuit of the CPU. A controller 61, an image obtainment processor 62, a patch position processor 63, and a color measurement processor 64 are functionally configured in the control processor 6 by the execution of the control processing program.

The controller 61 controls each unit of the color measuring device CM according to a function of the unit, and controls a whole of the color measuring device CM. More specifically, the controller 61 controls the sheet feeder 1, the sub-scanning direction movement unit (sheet conveyance unit) 2, the colorimetry unit 3, the main scanning direction movement unit 4, the imaging unit 5, the input unit 7, the output unit 8, the interface unit 9, and the storage unit 10, thereby controlling the operation of the color measuring device CM.

The image obtainment processor 62 obtains the image in the sheet of the measurement object such as the color chart CT using the imaging unit 5. More specifically, in the embodiment, because the imaging unit 5 includes a line sensor, the imaging unit 5 images the sheet of the measurement object while the sub-scanning direction movement unit (sheet conveyance unit) 2 conveys the sheet of the measurement object such as the color chart CT, whereby the image obtainment processor 62 obtains the image of the sheet of the measurement object. In the case that the color chart CT is accompanied with a predetermined code CD, the image obtainment processor 62 also obtains the image (second image) of the code CD by the similar operation using the imaging unit 5.

In controlling the operation of the color measuring device CM, the controller 61 obtains (decodes) the control information based on the second image of the code CD obtained by the image obtainment processor 62, and controls the operation of the color measuring device CM based on the obtained (decoded) control information.

The predetermined code CD is a transcription indicating the control information of the color measuring device CM. For example, the predetermined code CD is one of a one-dimensional code, a two-dimensional code, and a three-dimensional code. For example, the one-dimensional code is a bar code indicating information such as a number and a character by a width of a stripe pattern line, the two-dimensional code is a QR code (registered trademark) indicating information such as a number and a character by a shade of plurality of modules (dots) arrayed in a two-dimensional matrix, and the three-dimensional code is a color code indicating information such as a number and a character by an array of plurality of different colors (such as red, blue, and yellow). In the case that the predetermined code is the two-dimensional code or the three-dimensional code, the color measuring device CM is configured such that the position of the imaging unit 5 is two-dimensionally and relatively moved with respect to the sheet of the measurement object by using a movement unit. In the embodiment, as described above, the imaging unit 5 is provided so as to extend along the main scanning direction while the one direction that is of the array direction of the plurality of photoelectric conversion elements is aligned with the main scanning direction, and the sub-scanning direction movement unit (sheet conveyance unit) 2 moves the sheet of the measurement object along the sub-scanning direction. Accordingly, in the embodiment, the sub-scanning direction movement unit 2 corresponds to an example of the movement unit that relatively moves the position of the imaging unit 5 in a two-dimensional manner with respect to the sheet of the measurement object. In the embodiment, a QR code (registered trademark) CD is used as the code CD. The predetermined code CD may be drawn in the sheet of the color chart CT. In this case, because the code CD is drawn in the sheet of the color chart CT, the second image of the code CD can also be obtained in obtaining the first image of the color chart CT, and operation to obtain the image is completed at one time. Alternatively, the code CD is drawn in a second sheet separated from the sheet (first sheet) of the color chart CT, and the first sheet of the color chart CT and the second sheet of the code may be paired with each other. This case can deal with an increase in size of the code CD. Accordingly, the code indicating the control information having a larger capacity can be used compared with the case that the code CD is drawn in the sheet of the color chart CT.

Preferably, the control information indicated by the predetermined code CD includes color measurement control information about the control related to the colorimetry unit 3. For example, in measuring the color with the colorimetry unit 3, the color measurement control information includes at least one of exposure time information, exposure frequency information, moving speed information, ambient light source setting information, light source wavelength setting information, gain information, and output wavelength range information.

The exposure time information is information about time that light is received from the measurement object when the colorimetry unit 3 measures the color of the measurement object. The controller 61 controls the exposure time of the colorimetry unit 3, which allows resolution to be controlled in the colorimetry unit 3. Light and darkness and a color difference appear easily by lengthening the exposure time. On the other hand, a measurement time can be shortened by shortening the exposure time.

The exposure frequency information is information related to an exposure frequency of the measurement object in order to obtain one final measurement result when the colorimetry unit 3 measures the color of the measurement object. The controller 61 controls the exposure frequency of the colorimetry unit 3, and the exposure frequency is increased and measurement results are averaged, whereby a variation of measurement result can be suppressed. The controller 61 controls the exposure frequency of the colorimetry unit 3, and the exposure frequency is increased and measurement results are integrated, whereby the light and darkness and the color difference appear easily. On the other hand, the measurement time can be shortened by shortening the exposure frequency.

The moving speed information is information about a moving speed in at least one of the main scanning direction and the sub-scanning direction of the colorimetry unit 3. In the embodiment, the sub-scanning direction movement unit 2 conveys the sheet of the measurement object, and the colorimetry unit 3 relatively moves in the sub-scanning direction with respect to the sheet of the measurement object. Therefore, the moving speed in the sub-scanning direction of the colorimetry unit 3 becomes the moving speed of the sheet of the measurement object, and the controller 61 controls the sub-scanning direction movement unit 2, thereby controlling the moving speed in the sub-scanning direction of the colorimetry unit 3. The controller 61 controls the main scanning direction movement unit 4, thereby controlling the moving speed in the main scanning direction of the colorimetry unit 3. The measurement time can be shortened by increasing the moving speed. On the other hand, a vibration caused by repetition of drive and stop, a vertical variation, and degradation of position accuracy can be reduced by decreasing the moving speed.

The ambient light source setting information is information about a light source of a measurement environment of the colorimetry unit 3. For example, the ambient light source setting information is a D0 light source or a D1 light source. Because an object color depends on a light source color of an ambient light, the object color can more correctly be measured by setting the ambient light source.

The light source wavelength setting information is information about a wavelength of the light source of the colorimetry unit 3. The light source of the colorimetry unit 3 is configured with a plurality of light sources having different wavelength ranges or a partially overlapping wavelength range. The light source used in the measurement is switched under the control of the controller 61, which allows the measurement corresponding to a characteristic wavelength, the measurement of only a low-sensitivity wavelength, or the measurement that is not influenced by a specific wavelength.

The gain information is information about a gain of the colorimetry unit 3. Output of the colorimetry unit 3 is adjusted by the gain of the gain information under the control of the controller 61. The color of the measurement object is obtained based on the gain-adjusted output of the colorimetry unit 3.

The output wavelength range information is information designating the wavelength range of the measurement result output from the colorimetry unit 3. The wavelength range of the output wavelength range information is cut out from the output of the colorimetry unit 3 under the control of the controller 61. The color of the measurement object is obtained based on the output of the cut-out wavelength range of the colorimetry unit 3. When the output is performed in the wavelength range desired by the user, a data size of the output can be reduced while a user's demand is satisfied.

Preferably, the control information includes sheet feed control information about the control related to the sheet feeder 1. For example, the sheet feed control information includes at least one of order information sorting a plurality of color charts CT, information determining mixture of the color chart beyond expectation (unexpected), and management information managing the color chart.

For example, for a set chart in which the plurality of color charts CT are combined, the plurality of color charts CT are continuously and automatically measured, sometimes the order of the color charts CT is not normal order (original order) due to a human error. In such cases, the controller 61 can sort and output the measurement result of the colorimetry unit 3 by the order information indicated by the code CD, and can measure the plurality of color charts CT without concern for mounting order of the color chart CT.

For example, the color chart CT beyond expectation (unexpected, untargeted) can be mixed in measuring the plurality of color charts CT. In such cases, when the controller 61 determines that the information about the code CD is the information about the unintentional color chart CT (for example, an identifier (ID) of the color chart CT) in the measurement, controller 61 determines that the information about the code CD is beyond the expectation (unexpected) and it is possible to stop the measurement ,add the information about the code CD is beyond the expectation (unexpected) to the measurement data, or output the information about the code CD is beyond the expectation (unexpected) to the output unit 8.

The management information is information about date of producing the color chart CT or a management number of the color chart. In the color chart CT, generally decoloration is generated due to an influence of ambient light when time passes away since the production. Therefore, the controller 61 can determine the improper color chart CT based on the producing date in the management information about the code CD, and reliability of the measurement result is improved. The management number in the management information can also be used to distinguish the untargeted color chart CT.

Preferably the control information includes chart definition information including at least patch position definition information indicating the position of each of the plurality of patches in the color chart. The chart definition information is attribute information about the patch, and includes color information indicating the color of the patch in addition to the patch position definition information. The use of the chart definition information indicated by the code CD can correct the position of each patch of the patch position measurement information or compensate a missing patch in the measurement.

The predetermined code may include a network address such as an IP (Internet Protocol) address and a URL (Uniform Resource Locator) as one mode of the control information. In this case, the controller 61 may perform the control so as to obtain (decode) the network address based on the second image of the code CD obtained by the image obtainment processor 62, to obtain second control information stored in a network place corresponding to the obtained (decoded) network address, and to control the operation of the color measuring device CM based on the obtained second control information. Alternatively, the controller 61 may perform the control so as to store a color measurement result in the network place corresponding to the obtained network address.

The patch position processor 63 obtains patch position measurement information indicating a patch position (that is, the patch position) based on the image of the color chart CT obtained by the image obtainment processor 62. The patch position processor 63 may obtain the patch position measurement information based on the control information, such as the chart definition information, which is indicated by the predetermined code CD.

More specifically, for example, the patch position processor 63 generates binary horizontal edge image data and binary vertical edge image data for the horizontal direction (the main scanning direction, the X-direction) and the vertical direction (the sub-scanning direction, the Y-direction) by binarizing the image of the color chart CT with an edge filter used to detect an edge extending in one direction in the image, detects a horizontal edge line and a vertical edge line for the horizontal direction and the vertical direction by performing a Hough transform on the generated binary horizontal edge image data and binary vertical edge image data, and obtains a coordinate value (X,Y) of an intersection as patch position measurement information while each intersection in an intermediate line is set to each patch position. Preferably a plurality of disposition patterns in the chart region of the color chart CT are previously stored in the storage unit 10, the patch position processor 63 determines the disposition pattern corresponding to the color chart CT obtained by the image obtainment processor 62 from the plurality of disposition patterns previously stored in the storage unit 10, and detects the chart region from the image of the color chart CT obtained by the image obtainment processor 62 based on the determined disposition pattern, and obtains the patch position measurement information with respect to the detected chart region. Preferably the controller 61 corrects the patch position measurement information using the chart definition information obtained from the predetermined code CD, and obtains a more correct patch position. Therefore, for example, a deviation of the patch position is corrected, or a patch that is defined in not the patch position measurement information but the chart definition information can be compensated (covered).

The color measurement processor 64 relatively moves the position of the colorimetry unit 3 with respect to the color chart CT to each of the plurality of patch positions in the color chart CT based on the patch position measurement information obtained by the patch position processor 63 using the sub-scanning direction movement unit 2 and the main scanning direction movement unit 4, and the colorimetry unit 3 measures the color of each of the plurality of patches in the color chart CT.

Figure 5:
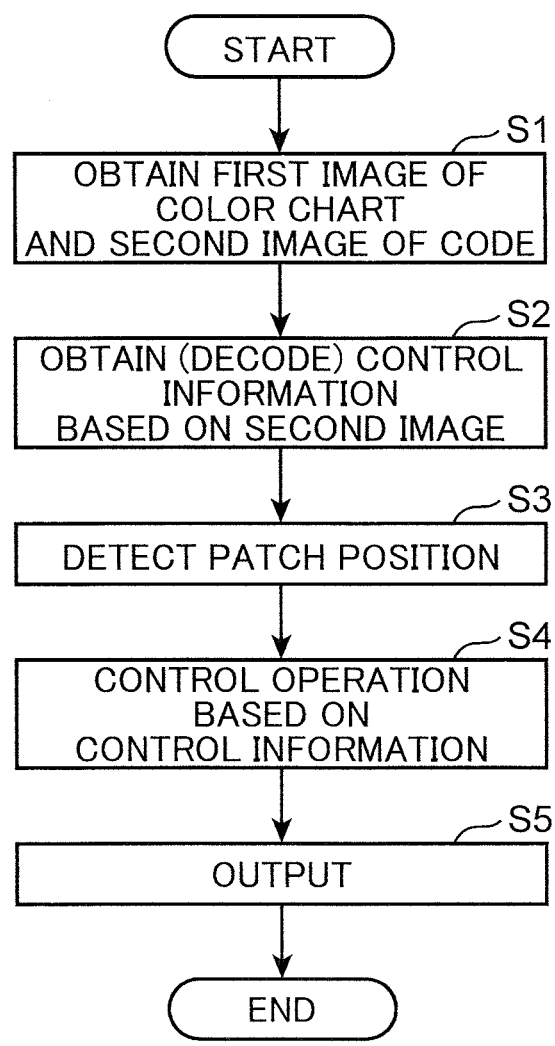
FIG. 5 is a flowchart illustrating a schematic operation of the color measuring device.
Figure 6A:
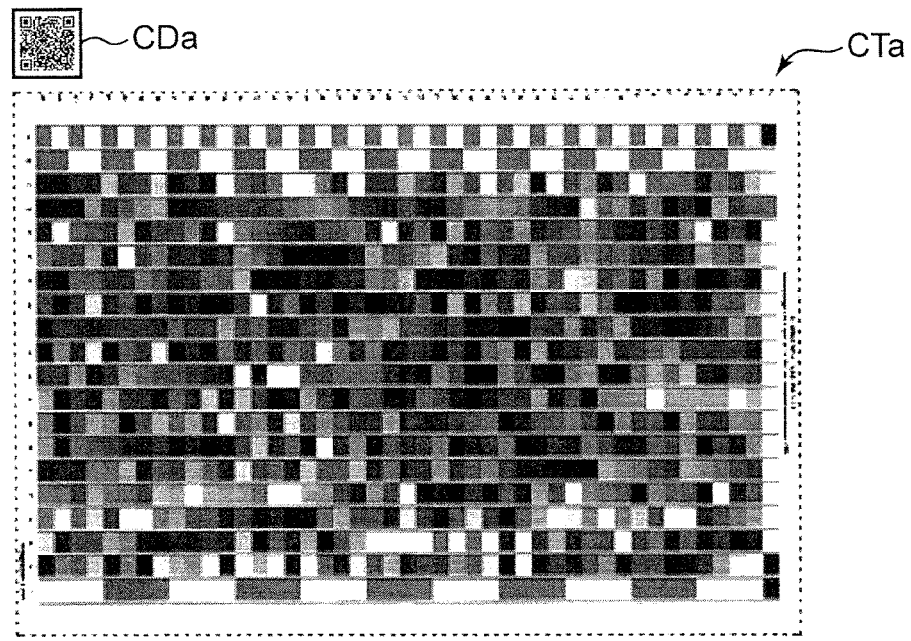
FIG. 6 is a view illustrating color charts of first and second modes by way of example.
Figure 6B:
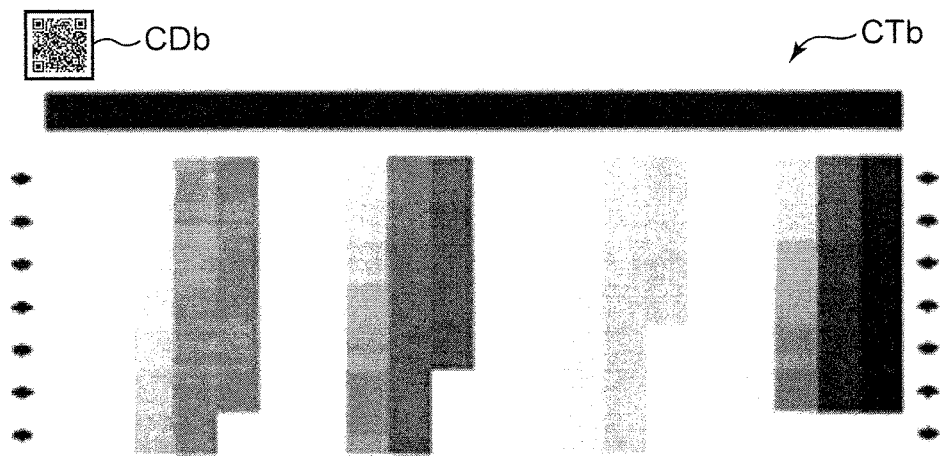
Figure 7A:
FIG. 7 is a view illustrating color charts of third and fourth modes by way of example.
Figure 7B:
Figure 8:
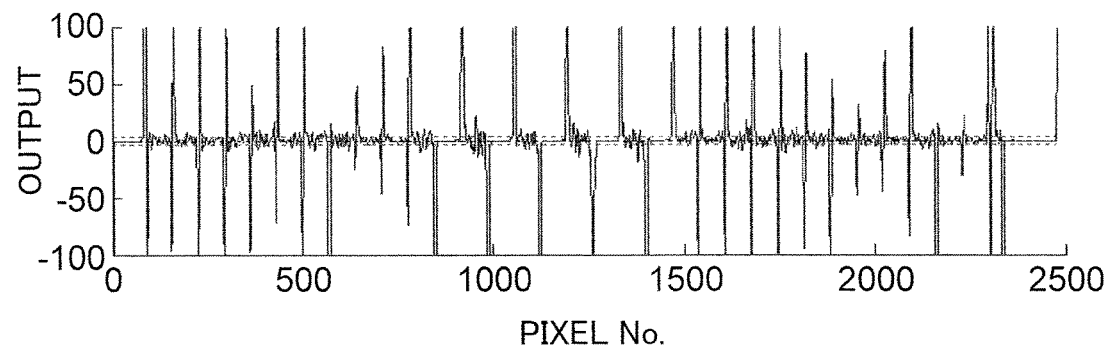
FIG. 8 is a view illustrating an example of a result of differential filtering, which is performed on an image of a certain position in a Y-direction at differential intervals of N points along a horizontal direction with respect to the color chart in FIG. 6A.
Figure 9:
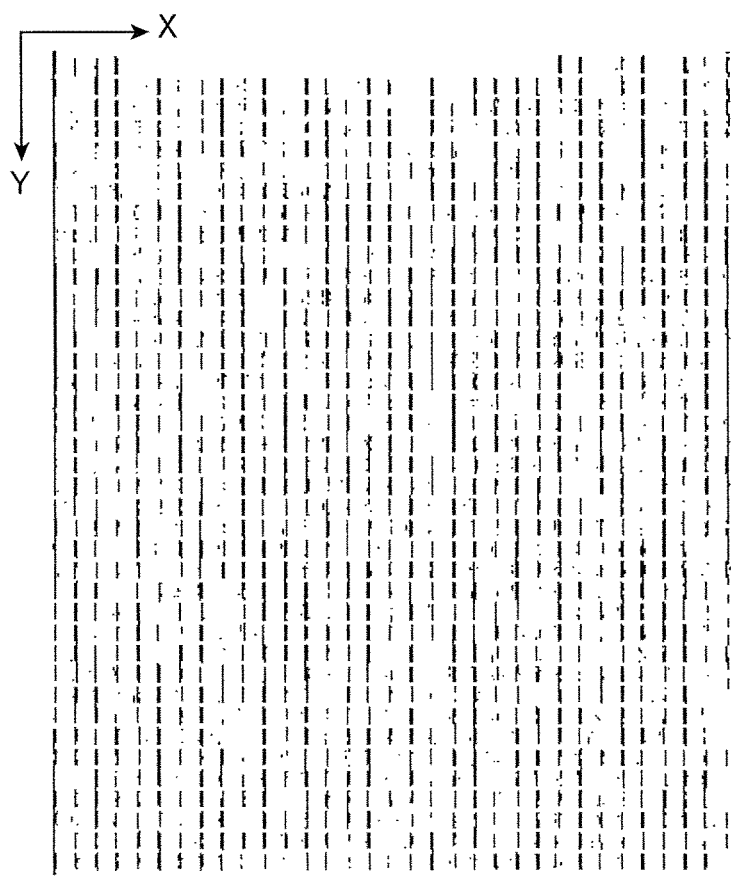
FIG. 9 is a view illustrating a binary vertical edge image of the color chart by way of example.
Figure 10:
FIG. 10 is a view illustrating a part of a vertical edge line of the color chart by way of example.
Figure 11:
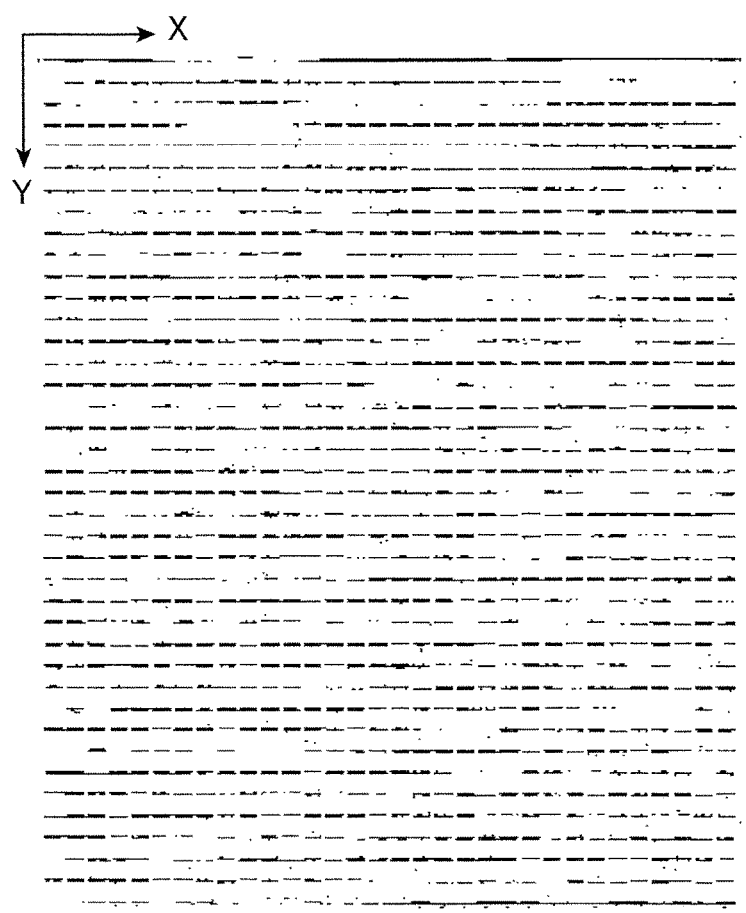
FIG. 11 is a view illustrating a binary horizontal edge image of the color chart by way of example.
Figure 12:
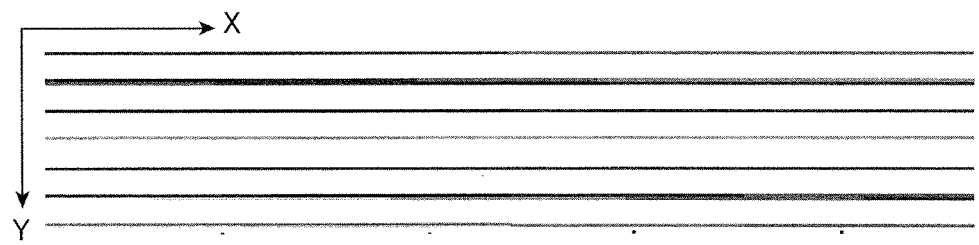
FIG. 12 is a view illustrating a part of a horizontal edge line of the color chart by way of example.
Figure 13:
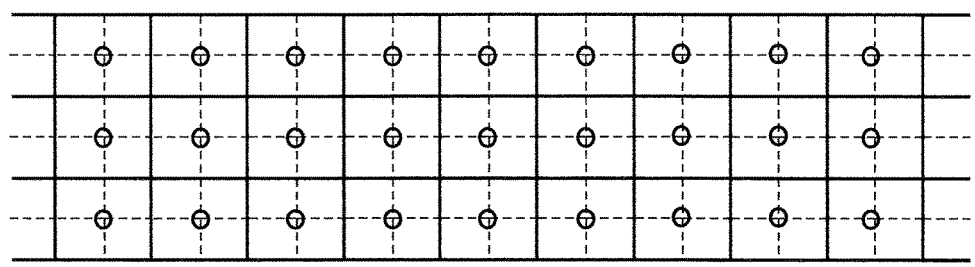
FIG. 13 is a view illustrating a part of each patch position obtained from the vertical edge line and horizontal edge line of the color chart by way of example.

An operation of the color measuring device of the embodiment will be described below. FIG. 5 is a flowchart illustrating a schematic operation of the color measuring device of the embodiment. FIG. 6 is a view illustrating color charts of first and second modes by way of example. FIG. 6A illustrates a color chart CTa of the first mode, and FIG. 6B illustrates a color chart CTb of the second mode. FIG. 7 is a view illustrating color charts of third and fourth modes by way of example. FIG. 7A illustrates a color chart CTc of the third mode, and FIG. 7B illustrates a color chart CTd of the fourth mode. FIG. 8 is a view illustrating an example of a result of differential filtering, which is performed on an image of a certain position in a Y-direction at differential intervals of N points along a horizontal direction with respect to the color chart in FIG. 6A. FIG. 9 is a view illustrating a binary vertical edge image of the color chart by way of example. FIG. 10 is a view illustrating a part of a vertical edge line of the color chart by way of example. FIG. 11 is a view illustrating a binary horizontal edge image of the color chart by way of example. FIG. 12 is a view illustrating a part of a horizontal edge line of the color chart by way of example. FIG. 13 is a view illustrating a part of each patch position obtained from the vertical edge line and horizontal edge line of the color chart by way of example. In FIG. 13, a solid line indicates the vertical edge line or the horizontal edge line, a broken line indicates an intermediate line between the vertical edge lines or an intermediate line between the horizontal edge lines, and a mark "o" indicates a measured patch position.

In the color measuring device CM, when the user (operator) turns on a power switch (not illustrated), the control processor 6 initializes each necessary unit, and the controller 61, the image obtainment processor 62, the patch position processor 63, and the color measurement processor 64 are functionally configured in the control processor 6 by the execution of the control processing program.

When measuring the color of each patch of the color chart CT, the color measuring device CM of the embodiment is roughly operated as follows. The color chart CT is set in the sheet feeder 1, and the input unit 7 issues an instruction to start the color measurement of the color chart CT. At this point, in the color measuring device CM, a whole image (first image) of the color chart CT and the image (second image) of the QR code CD are obtained in the forward conveyance by the image obtainment processor 62 as illustrated in FIG. 8 (S1, an image obtainment processing step). More specifically, the image obtainment processor 62 of the control processor 6 images the color chart CT and the code CD in each line along the main scanning direction (X-direction) using the imaging unit 5 in synchronization with the conveyance in the sub-scanning direction while conveying forward the sheet of the color chart CT in the sub-scanning direction (Y-direction) from one end to other end of the sheet of the color chart CT using the sub-scanning direction movement unit 2, thereby obtaining the whole image (first image) of the color chart CT and the second image of the code.

FIGS. 5 and 6 illustrate an example of the color chart CT accompanied with the code CD, the color chart CT being used in the color measuring device CM. For example, as illustrated in FIG. 6A, a color chart CTa of a first mode has a first disposition pattern in which the plurality of patches are arrayed in a random color arrangement such that a circumscribed figure (contour figure) of one chart region constructed with the plurality of patches becomes a quadrangle. The plurality of patches exist in the chart region. In the color chart CTa of the first mode, as illustrated in FIG. 6A, a code CDa, for example, a QR code (registered trademark) CDa is drawn in a region outside a chart region and on the upper left of the paper. For example, as illustrated in FIG. 6B, a color chart CTb of a second mode includes the plurality of patches, which are arrayed in a gradation color arrangement such that a circumscribed figure (contour figure) of one chart region becomes a quadrangle. The color chart CTb of the second mode includes a second disposition pattern including a black, rod-shape width position detection bar indicating a width of the chart region along the main scanning direction on one side (in the example of FIG. 6B, an upper side of a paper surface) outside the chart region and black, rhombic row position detection markers indicating the position of each row of the patch in the sub-scanning direction on both sides (in the example of FIG. 6B, right and left side of the paper surface) of the chart region outside the chart region. That is, in the second disposition pattern, the patches are disposed in an inside region surrounded by the width position detection bar and the row position detection markers. In the color chart CTb of the second mode, as illustrated in FIG. 6B, a code CDb, for example, a QR code (registered trademark) CDb is drawn in a region outside the chart region and on the upper left of the paper. For example, as illustrated in FIG. 7A, a color chart CTc of a third mode includes the plurality of patches, which are arrayed in a gradation color arrangement such that a circumscribed figure (contour figure) of one chart region becomes a long quadrangle. The color chart CTc of the third mode includes a third disposition pattern including an end marker, such as an L-shape, which indicates an end of the chart region at the end of the chart region. That is, in the third disposition pattern, the patches are disposed in an inside region surrounded by the end markers. In the color chart CTc of the third mode, as illustrated in FIG. 7A, a code CDc, for example, a QR code (registered trademark) CDc is drawn in a region outside the chart region and on the upper left of the paper. For example, as illustrated in FIG. 7B, a color chart CTd of a fourth mode includes the images and the color charts in a mixed manner, and the color chart CTd includes each patch in a first disposition pattern like the color chart CTa of the first mode. In the color chart CTd of the fourth mode, as illustrated in FIG. 7B, a code CDd, for example, a QR code (registered trademark) CDd is drawn in a region outside the chart region and on the upper left of the paper.

The codes CDa to CDd are drawn in a predetermined position such as the upper left of the paper in the sheet of the color chart CT as described above, which allows the color measuring device CM to easily detect the codes CDa to CDd. The codes CDa to CDd may be drawn at other predetermined positions such as an upper right or a lower left of the paper in the sheet of the color chart CT. In the case that the codes CDa to CDd are drawn on the upper left of the paper as described above, the color measuring device CM obtains the second image of the code CD in advance of the obtainment of the first image of the color chart, so that the control information based on the obtained second image of the code CD can directly be used to obtain the first image of the color chart. The code CD is not limited to the predetermined position, but may be any position. The code CD can detect a position determination marker owned by the code CD by a known technology.

Then, the color measuring device CM obtains (decodes) the control information based on the second image of the code CD obtained by the image obtainment processor 62 using the controller 61 of the control processor 6, and stores the obtained control information in the storage unit 10 (S2, a control information obtainment step (a control information decode step)).

Then, the color measuring device CM obtains the patch position measurement information (patch position) indicating the patch position based on the image of the color chart CT obtained by the image obtainment processor 62 with respect to each of the plurality of patches using the patch position processor 63 of the control processor 6, and stores the obtained patch position measurement information in the storage unit 10 (S3, a patch position detection step).

More specifically, for example, in the embodiment, the patch position processor 63 detects a vertical edge along the vertical direction (Y-direction) using a predetermined vertical edge detection edge filter based on the whole image of the color chart CT obtained by the image obtainment processor 62, and detects a horizontal edge along the horizontal direction (X-direction) using a predetermined horizontal edge detection edge filter. FIG. 8 illustrates an example of a result of differential filtering, which is performed on an image of a certain position in the Y-direction at differential intervals of N points along the X-direction with respect to the color chart in FIG. 6A. Then, the patch position processor 63 obtains an absolute value of the vertical edge after the edge filtering, compares the obtained absolute value to a previously set threshold, and binarizes the obtained absolute value, thereby generating image data of a binary vertical edge. For example, when the processing result after the edge filtering is binarized with respect to the image of the color chart CTa in FIG. 6A, the image data of the binary vertical edge image in FIG. 9 is generated. Similarly, the patch position processor 63 obtains an absolute value of the horizontal edge after the edge filtering, compares the obtained absolute value to a previously set threshold, and binarizes the obtained absolute value, thereby generating image data of a binary horizontal edge. For example, when the processing result after the edge filtering is binarized with respect to the image of the color chart CTa in FIG. 6A, the image data of the binary horizontal edge image in FIG. 11 is generated. Then, the patch position processor 63 performs the Hough transform on the image data of the binary vertical edge and the image data of the binary horizontal edge in the color chart CT, and detects the vertical edge line and the horizontal edge line. For example, when the Hough transform is performed on the image data of the binary vertical edge of the color chart CTa in FIG. 9, the vertical edge line in FIG. 10 is detected. For example, when the Hough transform is performed on the image data of the binary horizontal edge of the color chart CTa in FIG. 11, the horizontal edge line in FIG. 12 is detected. The patch position processor 63 obtains a vertical intermediate line that is of an intermediate line between the vertical edge lines adjacent to each other in each of the plurality of vertical edge lines, and similarly obtains a horizontal intermediate line that is of an intermediate line between the horizontal edge lines adjacent to each other in each of the plurality of horizontal edge lines, and obtains an intersection of each of the plurality of vertical intermediate lines and each of the plurality of horizontal intermediate lines as the patch position (X,Y). For example, the vertical intermediate line indicated by a broken line in FIG. 13 is obtained when the vertical intermediate line is obtained based on the vertical edge line obtained for the color chart CTa in FIG. 6A, the horizontal intermediate line indicated by a broken line in FIG. 13 is obtained when the horizontal intermediate line is obtained based on the horizontal edge line, and each intersection of the vertical intermediate line and the horizontal intermediate line is obtained as the patch position (X,Y) as indicated by a mark "o" in FIG. 13. In the embodiment, the position (X, Y) of each patch becomes the patch position measurement information.

The pieces of processing of obtaining the patch position measurement information may be performed after the chart region is detected. In the processing of detecting the chart region, the disposition pattern corresponding to the color chart CT obtained by the image obtainment processor 62 is determined from the plurality of disposition patterns previously stored in the storage unit 10, and the chart region is detected from the image of the color chart CT obtained by the image obtainment processor 62 based on the determined disposition pattern. Alternatively, a user may designate the chart region using the input unit 7.

Then, in the color measuring device CM, the controller 61 controls a predetermined operation of the color measuring device CM using the control information obtained in the processing S2 (S4, operation control step). For example, in measuring the color of each patch of the color chart CT, the controller 61 controls the operation of the color measuring device CM.

In the case that the control information about the code CD includes the chart definition information, the controller 61 corrects the patch position measurement information obtained in the processing S3 using the chart definition information obtained from the code CD, and obtains the more correct position of each patch. Therefore, for example, a deviation of the patch position is corrected, or a patch that is defined in not the patch position measurement information but the chart definition information can be compensated (covered).

Then, in the color measuring device CM, the color measurement processor 64 of the control processor 6 relatively moves the position of the colorimetry unit 3 with respect to the color chart CT to each of the plurality of patch positions in the color chart CT based on the patch position measurement information obtained in the processing S3 or the patch position measurement information corrected by the control information about the code CD as described above using the sub-scanning direction movement unit 2 and the main scanning direction movement unit 4, and the colorimetry unit 3 measures the color of each of the plurality of patches in the color chart CT (a color measurement step).

Various operations are controlled based on the control information about the code CD in measuring the color of each patch. For example, in the case that the control information includes color measurement control information about the control related to the colorimetry unit 3, the controller 61 controls the colorimetry unit 3 based on the color measurement control information. For example, in the case that the color measurement control information includes the exposure time information, the colorimetry unit 3 performs the exposure for the exposure time under the control of the controller 61. For example, in the case that the color measurement control information includes the exposure frequency information, the colorimetry unit 3 performs the exposure at the exposure frequency under the control of the controller 61. For example, in the case that the color measurement control information includes the moving speed information, the colorimetry unit 3 measures the color at the moving speed under the control of the controller 61. For example, in the case that the color measurement control information includes the ambient light source setting information, the colorimetry unit 3 measures the color with the ambient light source setting under the control of the controller 61. For example, in the case that the color measurement control information includes the light source wavelength setting information, the colorimetry unit 3 measures the color with the light source wavelength setting under the control of the controller 61. For example, in the case that the color measurement control information includes the gain information, the colorimetry unit 3 measures the color with the gain under the control of the controller 61. For example, in the case that the color measurement control information includes the output wavelength range information, the colorimetry unit 3 measures the color within the output wavelength range under the control of the controller 61.

On the other hand, in the case that the control information includes sheet feed control information about the control related to the sheet feeder 1, the controller 61 controls the operation of the sheet feeder 1 based on the sheet feed control information. For example, in the case that the sheet feed control information includes the order information sorting the plurality of color charts CT, the controller 61 sorts the measurement result of the colorimetry unit 3 using the order information indicated by the code CD. For example, in the case that the sheet feed control information includes the information determining the mixture of the color chart CT beyond expectation (unexpected), and the controller 61 determines that the information about the code CD is the information about the unintentional color chart CT (for example, an identifier (ID) of the color chart CT) in the measurement, the controller 61 determines that the information about the code CD is beyond the expectation (unexpected), and the controller 61 stops the measurement, adds the information about the code CD is beyond the expectation (unexpected) to the measurement data, or outputs the information about the code CD is beyond the expectation (unexpected) to the output unit 8. For example, in the case that the sheet feed control information includes management information managing the color chart CT, the controller 61 determines the improper color chart CT or the untargeted color chart CT based on the production date or management number of the management information about the code CD, and the controller 61 stops the measurement, adds the information that the color chart CT is the improper or untargeted color chart CT to the measurement data, or outputs the information that the color chart CT is the improper or untargeted color chart CT to output unit 8.

In the color measuring device CM, when the color measurement processor 64 measures the color of the final patch, the controller 61 of the control processor 6 outputs the measured color of the patch to the output unit 8, and the processing is ended (S5, an output step). As needed, the controller 61 of the control processor 6 may output the measured color of the patch to an external device through the interface unit 9.

As described above, in the color measuring device CM of the embodiment and the color measuring method incorporated in the color measuring device CM, the imaging unit 5 obtains not only the first image of the color chart CT but also the second image of the code CD. Accordingly, in the color measuring device CM and the color measuring method, because the second image of the code can be obtained by the color measuring device CM of itself by the diversion of the imaging unit 5 that originally obtains the first image of the color chart CT, it is not necessary to provide the scanner that obtains the second image of the code CD unlike the system disclosed in Patent Literature 1, but a simpler configuration is obtained. In the color measuring device CM and the color measuring method, the control information is obtained (decoded) based on the second image of the code CD obtained by the image obtainment processor 62 using the imaging unit 5, and the operation of the color measuring device CM is controlled based on the obtained (decoded) control information, so that the control information about the code CD can surely be used. Accordingly, in the color measuring device CM and the color measuring method, the information about the code CD can surely be used with a simple configuration.

In the color measuring device CM of the embodiment and the color measuring method incorporated in the color measuring device CM, in the case that the control information includes the color measurement control information, the color can properly be measured because the control related to the colorimetry unit 3 is performed using the color measurement control information about the code CD.

In the color measuring device CM of the embodiment and the color measuring method incorporated in the color measuring device CM, in the case that the control information includes the chart definition information, the color of each patch can be measured at a more correct position because the position of each patch indicated by the patch position definition information in the chart definition information about the code CD is used.

In the color measuring device CM of the embodiment and the color measuring method incorporated in the color measuring device CM, in the case that the control information includes the sheet feed control information, the color can properly be measured because the control related to the sheet feeder 1 is performed using the sheet feed control information about the code CD.

In the embodiment, the color measuring device CM includes the imaging unit 5 including the line sensor in which the plurality of photoelectric conversion elements are arrayed in one direction. Alternatively, instead of the imaging unit 5, the color measuring device CM may include an imaging unit including an area sensor (two-dimensional image sensor) in which the plurality of photoelectric conversion elements are two-dimensionally arrayed in two directions (for example, two directions orthogonal to each other) linearly independent of each other. The imaging unit including the area sensor can take the whole image of the color chart CT without conveying the color chart CT.

In the embodiment, the movement of the position of colorimetry unit 3 with respect to the sheet of the measurement object is performed by the movement of the colorimetry unit 3 along the main scanning direction using the main scanning direction movement unit 4 and by the movement of the sheet of the measurement object along the sub-scanning direction using the sub-scanning direction movement unit 2. However, the present invention is not limited to the above. Alternatively, for example, the movement unit that relatively moves the position of colorimetry unit 3 with respect to the sheet of the measurement object may be a movement mechanism that moves the colorimetry unit 3 in the main scanning direction and the sub-scanning direction with respect to the sheet of the measurement object placed on the stage in a resting state or an XY-stage that moves in the main scanning direction and the sub-scanning direction with respect to the fixed colorimetry unit 3 while the sheet of the measurement object is placed on the XY-stage. For example, the movement unit may move the colorimetry unit 3 in one of the main scanning direction and the sub-scanning direction, and move the stage in the other direction. The imaging unit including the area sensor is suitable for the movement unit having this configuration.

The description discloses technologies of various mode as described above, and the main technologies are summarized as follows.

According to an aspect, a color measuring device includes: a colorimetry unit that measures color; an imaging unit that takes an image; a movement unit that relatively moves a position of the colorimetry unit with respect to the sheet of the measurement object; an image obtainment processor that obtains a first image of a color chart and a second image accompanied with the color chart using the imaging unit, the color chart including plurality of patches each of which is a region of a predetermined color, the second imager being a predetermined code indicating control information about the color measuring device; and a controller that controls operation of the color measuring device by controlling the colorimetry unit, the imaging unit, and the movement unit. The controller obtains the control information based on the second image obtained by the image obtainment processor, and controls the operation of the color measuring device based on the obtained control information.

In the color measuring device, not only the first image of the color chart but also the second image of the code are obtained by the imaging unit. Accordingly, in the color measuring device, because the second image of the code can be obtained by the color measuring device of itself by diversion of the imaging unit that originally obtains the first image of the color chart, it is not necessary to provide the scanner that obtains the second image of the code unlike the system disclosed in Patent Literature 1, but the simpler configuration is obtained. In the color measuring device, the control information is obtained (decoded) based on the second image of the code obtained by the image obtainment processor using the imaging unit, and the operation of the color measuring device is controlled based on the obtained (decoded) control information, so that the control information about the code can surely be used. Accordingly, in the color measuring device, the code information can surely be used with a simple configuration.

According to another aspect, in the color measuring device, the control information includes color measurement control information about the control related to the colorimetry unit. Preferably, in measuring the color with the colorimetry unit 3, the color measurement control information includes at least one of exposure time information, exposure frequency information, moving speed information, ambient light source setting information, light source wavelength setting information, gain information, and output wavelength range information.

The color measuring device can properly measure the color because the control related to the colorimetry unit can be performed using the color measurement control information about the code.

According to another aspect, in the color measuring device, the control information includes chart definition information including at least patch position definition information indicating a position of each of the plurality of patches in the color chart.

In the color measuring device, the color of each patch can be measured at a more correct position because the patch position indicated by the patch position definition information in the chart definition information about the code.

According to another aspect, the color measuring device further includes a sheet feeder that feeds the sheet of the measurement object to the movement unit. The controller controls the sheet feeder, and the control information includes sheet feed control information about the control related to the sheet feeder. Preferably, the sheet feed control information includes at least one of the order information sorting the plurality of color charts, the determination information determining the mixture of the color chart beyond expectation (unexpected), and the management information managing the color chart.

The color measuring device can properly measure the color because the control related to the sheet feeder can be performed using the sheet feed control information about the code.

According to another aspect, in the color measuring device, the predetermined code is drawn in a sheet of the color chart.

In the color measuring device, because the code is drawn in the sheet of the color chart, the second image of the code can also be obtained in obtaining the first image of the color chart, and the operation to obtain the image is completed at one time.

According to another aspect, in the color measuring device, the predetermined code is drawn in a second sheet separated from a sheet of the color chart, and the sheet of the color chart and the second sheet are paired with each other.

A size (area) of the code increases when the data capacity of control information indicated by the code increases. In the color measuring device, the code is drawn in the second sheet separated from the sheet of the color chart, so that the increase in size of the code can be dealt with. Accordingly, the code indicating the control information having a larger capacity can be used compared with the case that the code is drawn in the sheet of the color chart.

According to another aspect, in the color measuring device, the predetermined code is one of a one-dimensional code, a two-dimensional code, and a three-dimensional code, and when the predetermined code is the two-dimensional code or the three-dimensional code, the movement unit two-dimensionally and relatively moves a position of the imaging unit with respect to the sheet of the measurement object. Preferably, for example, the one-dimensional code is a bar code. Preferably, for example, the two-dimensional code is a QR code (registered trademark). Preferably, for example, the three-dimensional code is a color code.

Therefore, the color measuring device in which one of the one-dimensional code, the two-dimensional code, and the three-dimensional code is used can be provided.

According to another aspect, a color measuring method for a color measuring device including: a colorimetry unit that measures color; an imaging unit that takes an image; a movement unit that relatively moves a position of the colorimetry unit with respect to the sheet of the measurement object; and a controller that controls operation of the color measuring device by controlling the colorimetry unit, the imaging unit, and the movement unit, the color measuring method includes: an image obtainment processing step of obtaining a first image of a color chart and a second image accompanied with the color chart using the imaging unit, the color chart including plurality of patches each of which is a region of a predetermined color, the second color being a predetermined code indicating control information about the color measuring device; an obtainment step of obtaining the control information based on the second image obtained in the image obtainment processing step; and a control step of controlling operation of the color measuring device based on the control information obtained in the obtainment step.

In the color measuring method, not only the first image of the color chart but also the second image of the code are obtained by the imaging unit. Accordingly, in the color measuring method, because the second image of the code can be obtained by the color measuring device of itself by diversion of the imaging unit that originally obtains the first image of the color chart, it is not necessary to provide the scanner that obtains the second image of the code unlike the system disclosed in Patent Literature 1, but a simpler configuration is obtained. In the color measuring method, the control information is obtained (decoded) based on the second image of the code obtained by the image obtainment processing step using the imaging unit, and the operation of the color measuring device is controlled based on the obtained control information, so that the control information about the code can surely be used. Accordingly, in the color measuring method, the code information can surely be used with a simple configuration.

This application is based on and claims the benefit of priority from Japanese Patent Application No. 2015-77705, filed on Apr. 6, 2015, the entire contents of which are incorporated herein by reference.

While the embodiment of the present invention is properly and adequately described with reference to the drawings, it is noted that those skilled in the art can easily change and/or modify the embodiment. Accordingly, as long as the change or modification made by those skilled in the art does not depart from the scope of the present invention, the change or modification is included in the scope of the present invention.

INDUSTRIAL APPLICABILITY

The present invention can provide the color measuring device and the color measuring method.

The invention claimed is:
1. A color measuring device comprising:
a colorimetry unit that measures color;
an imaging unit that takes an image;
a movement unit that relatively moves a position of the colorimetry unit with respect to a sheet of a measurement object;
an image obtainment processor that obtains a first image of a color chart and a second image accompanied with the color chart using the imaging unit, the color chart including a plurality of patches each of which is a region of a predetermined color, the second image being a predetermined code indicating control information about the color measuring device; and a controller that controls automatic operation of the color measuring device based on the predetermined code by controlling the colorimetry unit, the imaging unit, and the movement unit, for making color measurements, wherein the controller obtains the control information, based on the second image obtained by the image obtainment processor, and controls the automatic operation of the color measuring device, based on the obtained control information.

2. The color measuring device according to claim 1, wherein the control information includes color measurement control information about the control related to the colorimetry unit.

3. The color measuring device according to claim 1, wherein the control information includes chart definition information including at least patch position definition information indicating a position of each of the plurality of patches in the color chart.

4. The color measuring device according to claim 1, further comprising a sheet feeder that feeds the sheet of the measurement object to the movement unit, wherein the controller controls the sheet feeder, and the control information includes sheet feed control information about the control related to the sheet feeder.

5. The color measuring device according to claim 1, wherein the predetermined code is drawn in a sheet of the color chart.

6. The color measuring device according to claim 1, wherein the predetermined code is drawn in a second sheet separated from a sheet of the color chart, and the sheet of the color chart and the second sheet are paired with each other.

7. The color measuring device according to claim 1, wherein the predetermined code is one of a one-dimensional code, a two-dimensional code, and a three-dimensional code, and when the predetermined code is the two-dimensional code or the three-dimensional code, the movement unit two-dimensionally and relatively moves a position of the imaging unit with respect to the sheet of the measurement object.

8. A color measuring method for a color measuring device including: a colorimetry unit that measures color; an imaging unit that takes an image; a movement unit that relatively moves a position of the colorimetry unit with respect to a sheet of a measurement object; and a controller that automatically controls operation of the color measuring device based on a predetermined code by controlling the colorimetry unit, the imaging unit, and the movement unit, for making color measurements, the color measuring method comprising:

an image obtainment processing step of obtaining a first image of a color chart and a second image accompanied with the color chart using the imaging unit, the color chart including a plurality of patches each of which is a region of a predetermined color, the second image being the predetermined code indicating control information about the color measuring device;

an obtainment step of obtaining the control information based on the second image obtained in the image obtainment processing step; and a control step of automatically controlling operation of the color measuring device based on the control information obtained in the obtainment step.

9. The color measuring device according to claim 1, wherein the controller controls operation of the movement unit based on the obtained control information.

10. The color measuring method according to claim 8, wherein, in the control step, operation of the movement unit is controlled based on the obtained control information.

* * * * *